(12) United States Patent
Snow

(10) Patent No.: US 6,673,058 B2
(45) Date of Patent: Jan. 6, 2004

(54) TEMPORARY DILATING TIP FOR GASTRO-INTESTINAL TUBES

(75) Inventor: Todd Snow, Carmel, IN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/885,492

(22) Filed: Jun. 20, 2001

(65) Prior Publication Data

US 2002/0198440 A1 Dec. 26, 2002

(51) Int. Cl.[7] .............................................. A61M 31/00
(52) U.S. Cl. ........................ 604/506; 604/910; 604/270; 128/898
(58) Field of Search ....................... 604/910, 92, 238, 604/93.01, 257, 261, 270, 105, 175, 164.05, 174; 600/129, 115, 114, 121, 127; 128/898

(56) References Cited

U.S. PATENT DOCUMENTS

| | | | |
|---|---|---|---|
| 3,736,939 A | * | 6/1973 | Taylor .......................... 604/265 |
| 4,315,513 A | | 2/1982 | Nawash et al. |
| 4,393,873 A | | 7/1983 | Nawash et al. |
| 4,698,056 A | * | 10/1987 | Ciannella ................ 604/164.02 |
| 4,834,725 A | | 5/1989 | Iwatschenko |
| 4,863,438 A | | 9/1989 | Gauderer et al. |
| 4,900,306 A | | 2/1990 | Quinn et al. |
| 4,944,732 A | * | 7/1990 | Russo .......................... 604/105 |
| 5,049,138 A | * | 9/1991 | Chevalier et al. ........... 604/265 |
| 5,205,830 A | | 4/1993 | Dassa et al. |
| 5,248,302 A | | 9/1993 | Patrick et al. |
| 5,401,257 A | | 3/1995 | Chevalier, Jr. et al. |
| 5,931,776 A | | 8/1999 | Dotolo |
| 5,941,855 A | | 8/1999 | Picha et al. |
| 6,077,250 A | | 6/2000 | Snow et al. |
| 6,332,877 B1 | * | 12/2001 | Michels ....................... 604/270 |
| 6,381,495 B1 | * | 4/2002 | Jenkins ........................ 607/115 |

OTHER PUBLICATIONS

"D'Agostino/vanSonnenberg Gastrojejunal™ Catheters with TempTip™ Dissolving Tip and Kits," New Product Bulletin, Medi–Tech® Boston Scientific Corporation (2 pages) ©1995 Boston Scientific Corporation.

"Flexima™ Hydrophilic Drainage Catheters—TempTip™" Brochure, Medi–Tech® Boston Scientific Corporation (4 pages), ©1996 Boston Scientific Corporation.

"Non–Vascular Interventional Products," Ordering Information Brochure, Boston Scientific Medi–Tech® (3 pages), ©1998 Boston Scientific Corporation.

U.S. patent application Ser. No. 09/252,407 (allowed), entitled "Gastro–Intestinal Tube Placement Device."

U.S. patent application Ser. No. 09/568,044, entitled, "Apparatus and Method for Percutaneously Placing Gastrostomy Tubes."

* cited by examiner

Primary Examiner—Brian L. Casler
Assistant Examiner—Matthew F DeSanto
(74) Attorney, Agent, or Firm—William J. Shaw

(57) ABSTRACT

A percutaneous endoscopic gastrostomy device comprises a removable, dilating tip. The tip is located at the distal end of the device and provides for tissue dilation upon entry of the device into the body of a patient. The tip is lubricious and biodegradable. The tip is removable by dislodging it from the end of the device following placement of the device in the patient. The tip is usually dislodged by action of a physician to dislodge the tip, however it may be dissolved by application of a biocompatible solvent or through digestion. Following removal of the tip from the device, the tip is dissolved naturally by digestion.

2 Claims, 18 Drawing Sheets

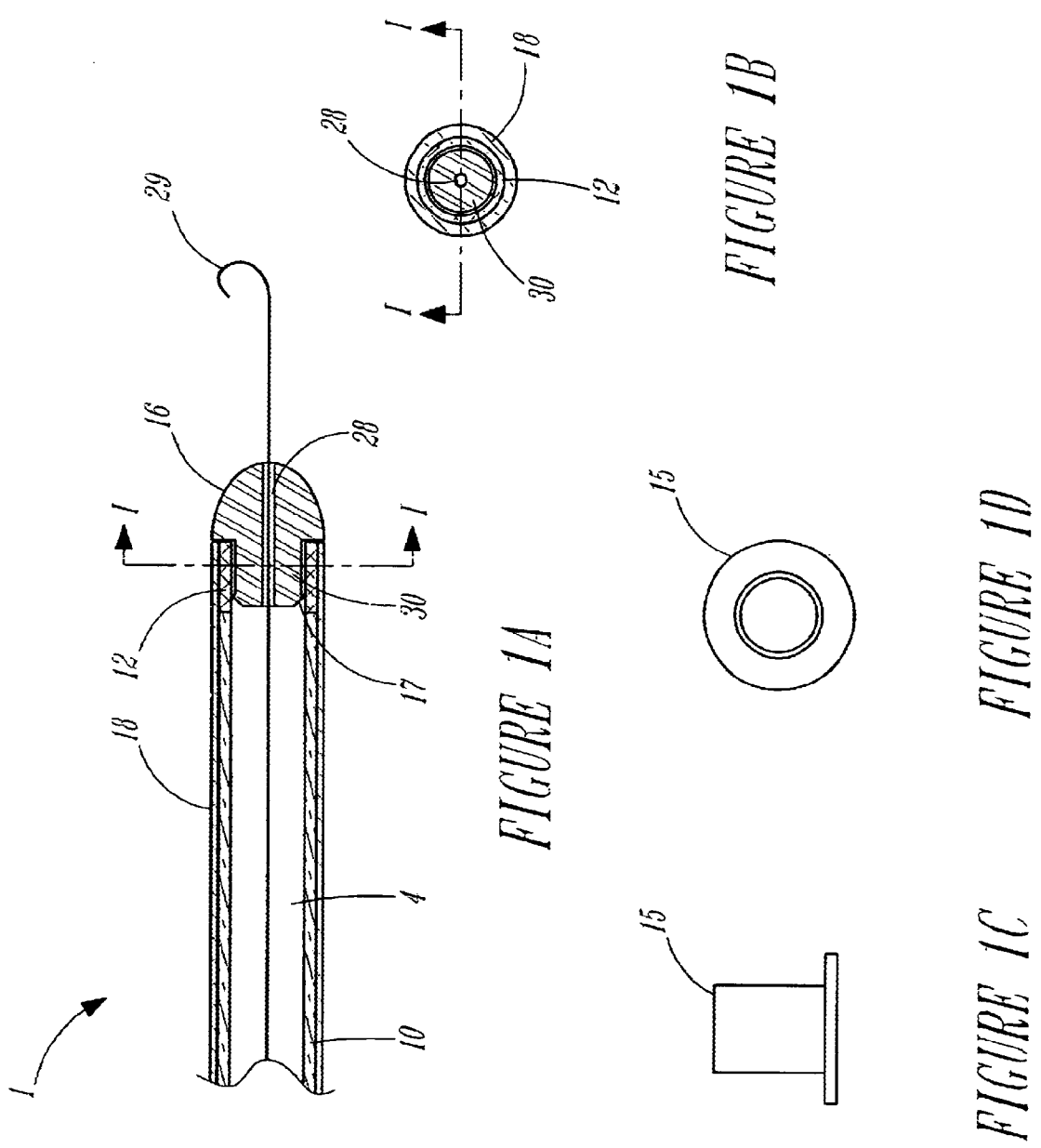

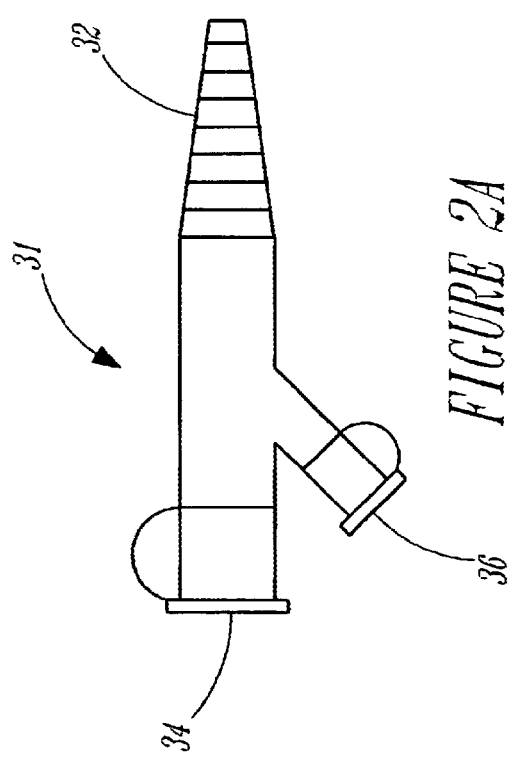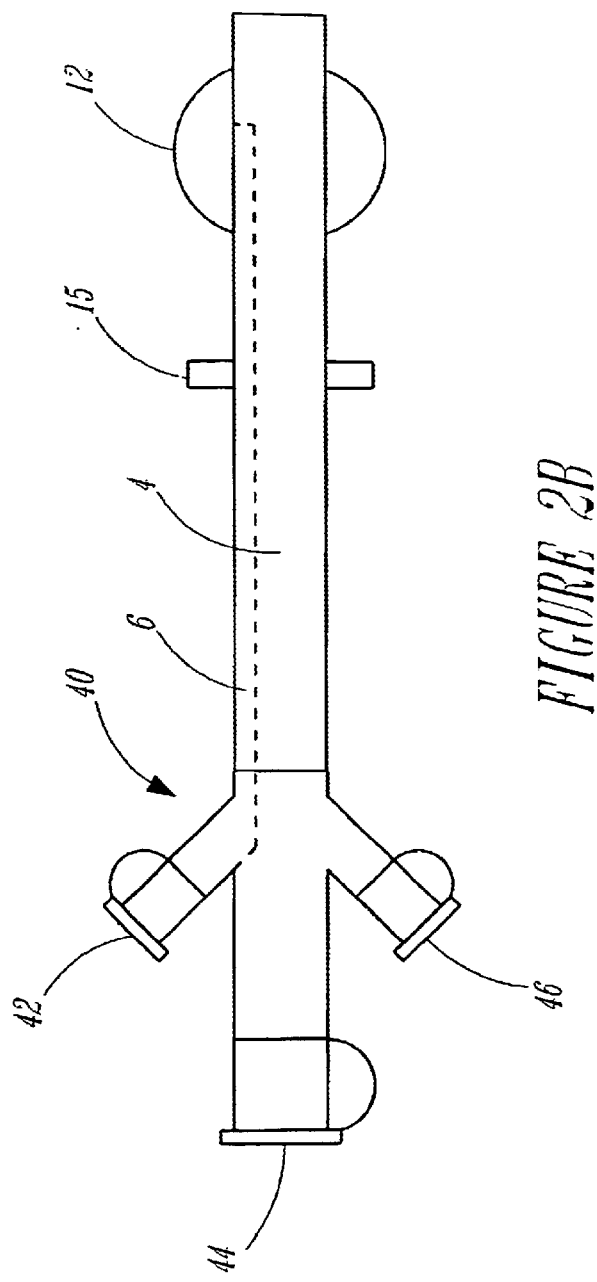

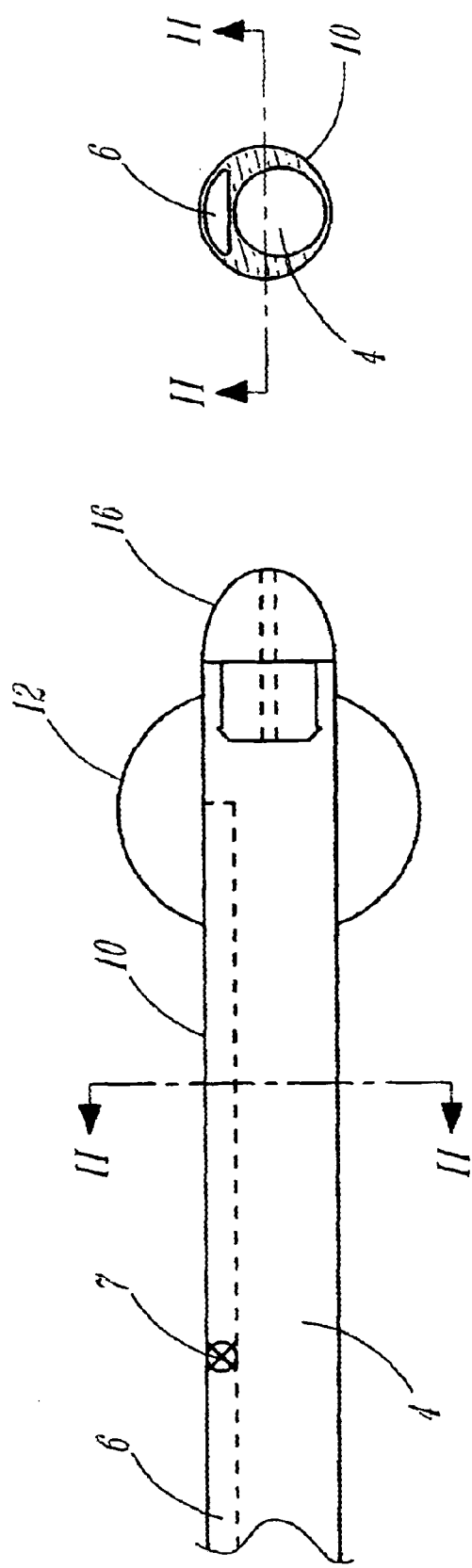

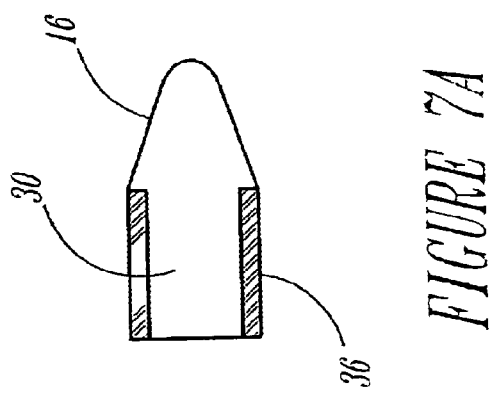
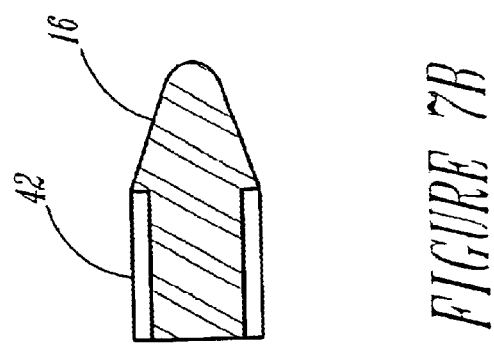
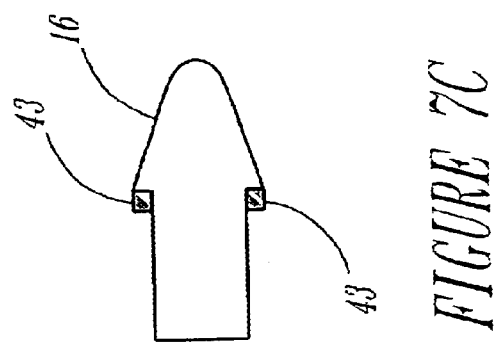

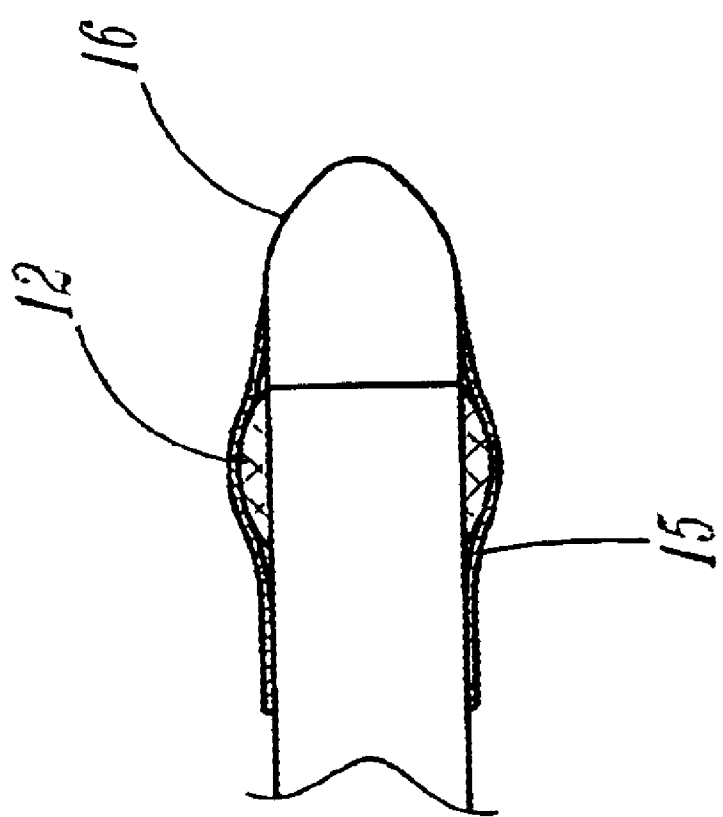

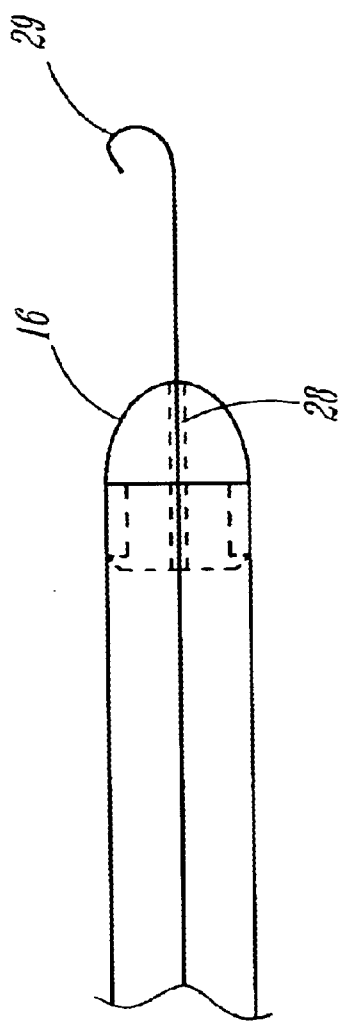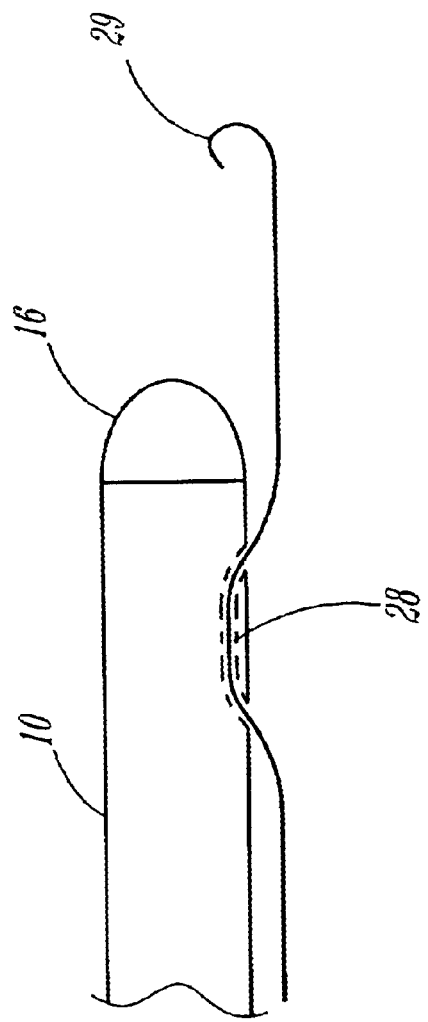

TEMPORARY DILATING TIP FOR GASTRO-INTESTINAL TUBES

BACKGROUND OF THE INVENTION

A PEG procedure, or Percutaneous Endoscopic Gastrostomy, involves placing a tube percutaneously through the abdomen and into the stomach of a patient to provide a feeding port for a patient who cannot swallow. A similar procedure is known as Percutaneous Endoscopic Jejunostomy or PEJ where the system is placed into the jejunum. This device may be used for a host of reasons including administering food or drugs, allowing drainage of the body or providing a surgical access port. The PEG tube resides in place for a few months at a time and allows the practitioner to access the stomach from outside the body. The tube is usually replaced over time, typically every three months.

Initial placement of PEG devices will vary depending upon the device design, condition of the patient and the medical professional's preferred technique. Most designs rely on anchoring one end of the PEG system inside the body and one end outside the body. More specifically, a bolster is incorporated at the distal end of the PEG tube, which is internal to patient. This bolster may be a balloon or a flexible disk positioned annularly around the outside edge of the tube. The bolster is designed to be delivered in a constricted state and once in position within the body, deployed in an expanded state. The bolster may dictate how the PEG is placed. For example, a rigid disk could not go into the body through a small hole, so the PEG may be introduced into the patient's mouth through the esophagus, into the stomach, and out through the abdomen. If the bolster is collapsed or collapsible, then the PEG may be placed percutaneously in a pushing manner.

Once a PEG device is positioned within a patient, it remains in place until such a time as the practitioner decides that it should be replaced or that the treatment has ended. Replacement is typically effected by removing the initial PEG tube, by tugging it out of the fistula or wound track, and pushing in a new PEG system. There are often no other tools involved. Advancement of the replacement PEG to the correct position may be hindered as a result of many factors such as the tortuous fistula path, a shrunken fistula, and the column strength of the PEG tube. As a result, the PEG tube may not advance very easily and a smaller PEG tube may have to be used. Smaller diameter PEGs tend to clog more frequently and eventually need replacement. This size reduction cycle can continue as PEGs are removed and replaced over months until the procedure is not practical.

Current PEG replacement systems are not optimized for placement within the body of a patient. The medical field is in need of a PEG replacement tube that can be placed quickly and accurately into the initial PEG fistula with minimal pain and trauma to the patient. The preferred device would maintain the initial stoma size and be placed accurately.

BRIEF DESCRIPTION OF THE DRAWINGS

FIG. 1 Illustrates an embodiment of the invention.

FIG. 2 Illustrates an alternate embodiment of the invention.

FIG. 7 Illustrates an alternate embodiment of the tip component of the invention.

FIG. 13 Illustrates an alternate embodiment of the invention.

SUMMARY OF THE INVENTION

Figure 3:
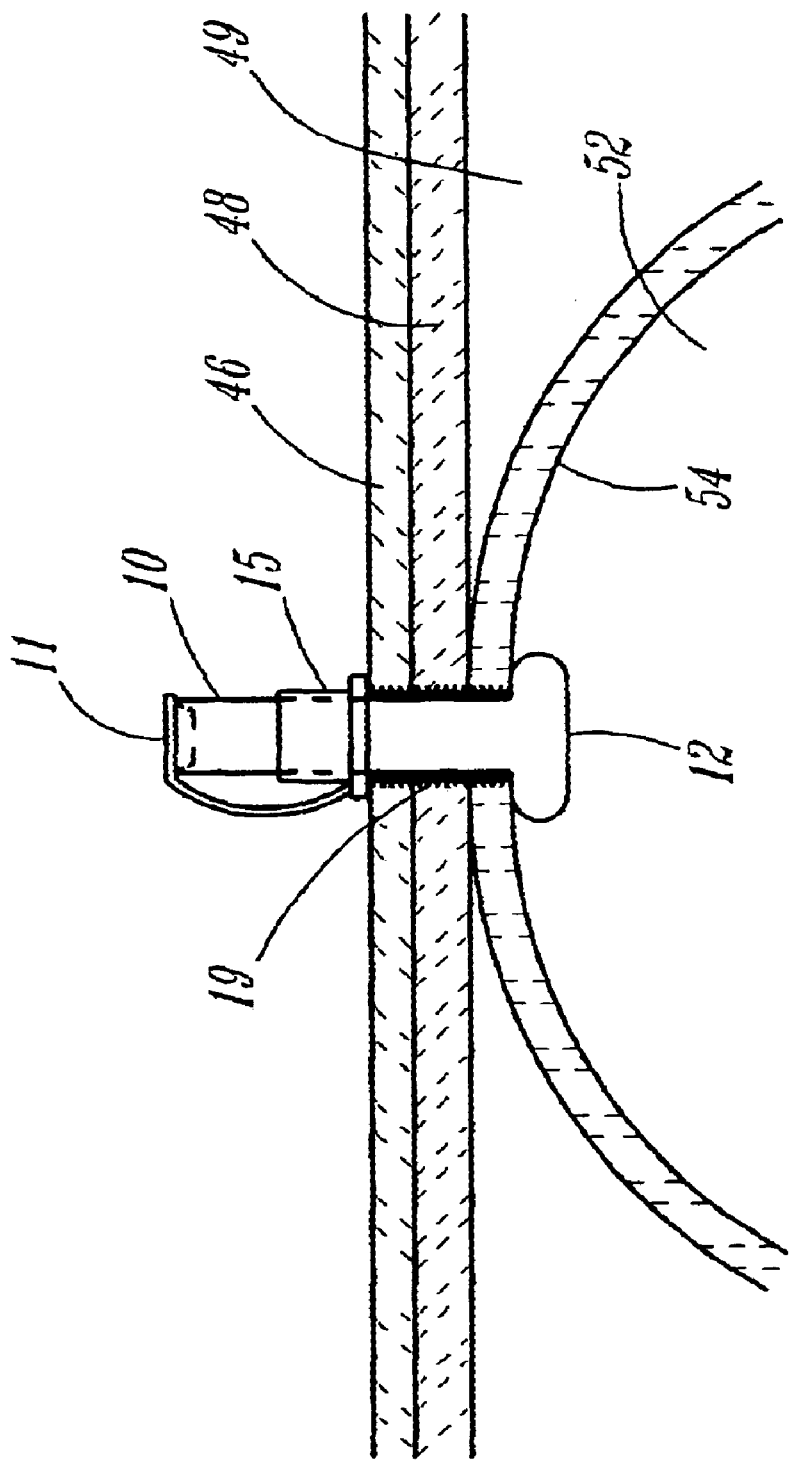
FIG. 3 Illustrates the invention in the body of a patient.

The invention relates to devices for delivering a PEG system into the body of a patient. In one embodiment the invention relates to systems to facilitate the replacement of a PEG into a fistula created by the previous PEG. In other embodiments the invention provides devices and methods for dilating the fistula as the PEG system is advanced into the body.

In one embodiment, a PEG system includes a removable, lubricious, biodegradable, dilating tip member inserted within the distal end of the PEG. A guidewire is utilized. The tip may have a central lumen running along its axis to permit the deployment of the replacement PEG over the guidewire. The bolster of the PEG system may be retained beneath a sheath during forward deployment of the device through tissues. Once positioned, the sheath may be removed to deploy the internal bolster and the tip may be removed by applying force against it relative to the distal end of the tube.

In one embodiment, The PEG system comprises a gelatin dilating tip. The tip may be formed to lie over the bolster of the PEG, providing both a dilating device on the end of the PEG and a retention system for the bolster. The gelatin tube may be lubricious upon advancement. The gelatin tip may be biodegradable and may dissolve quickly within the body to release the bolster and secure the PEG.

DETAILED DESCRIPTION

FIGS. 1A and 1B illustrate an embodiment of the distal portion of PEG system 1 of the present invention. PEG system 1 is shown to include single lumen 4 internal to PEG body 10. PEG system 1 includes an internal bolster 12 which is contained by a sheath 18 while in a non-deployed state. Bolster 12 of the single lumen system as illustrated must be a solid bolster and not a balloon, as a balloon requires a second inflation lumen. As PEG system 1 has only one internal lumen 4, the length of the PEG body 10 may be trimmed to an optimal length once the system is in place in the body. The optimal length allows at least 2 in. to be left external to the abdomen of the patient. The distal tip of PEG system 1 includes a temporary dilating tip 16. Tip 16 further includes guidewire lumen 28 and attachment 30. Body 10 includes a biocompatible, polymeric tube. PEG system 1 further includes an external bolster 15 as illustrated in FIGS.

1C and 1D for securing the system to the body of the patient. A guidewire 29 is included with PEG system 1.

The proximal or external end of PEG system 1 is then capped with a removable cap, clamped or fitted with an attachable hub 30 as is illustrated in FIG. 2A. Attachable hub 30 includes connector 32, food port 34 and second port 36. Second port 36 may be used to add saline or drugs and the like before, during or after use of food port 34 for delivering nutritional solutions. Ports 34 and 36 join together in hub 30 to feed into lumen 4 of PEG system 1. PEG system 1 may also be provided as the embodiment illustrated in FIG. 2B. In this embodiment, hub 40 is already attached to PEG body 10. This system allows for more than one lumen in the PEG system as the ports connect directly to their respective lumens. This embodiment also ensures a seal between the ports and the lumens that they feed. A balloon bolster 12 can be used with the system of FIG. 2B as the balloon may be inflated through port 42 and lumen 6 and remain inflated. FIG. 2B illustrates a PEG system with a balloon internal bolster 12, inflation lumen 6, feeding lumen 4, hub 40 and port 42 for inflating the balloon, port 44 for administering food and port 46 for administering saline, drugs and the like 46. Inflation port 6 can be sealed off with a removable cap, a clamp an internal valve or a luer lock system. Ports 44 and 46 both feed into the lumen 4 through hub 40.

FIGS. 2C and 2D illustrate an alternate embodiment where a second lumen 6 is incorporated in PEG body 10. Second lumen 6 serves as an inflation lumen for internal balloon bolster 12. Inflation port 6 may have a sealing valve 7 to maintain fluid pressure within the bolster following inflation. Valve 7 is opened by inserting a needle or hypotube attached to the end of an inflation syringe used to deliver saline to the balloon. Port 6 may also have a locking system such as a luer lock which mates with a component of the syringe distal end to establish a fluid seal during bolster inflation. An alternative embodiment to the location of valve 7 is to have valve 7 located in the hub of PEG system 1, for example, within port 42 of FIG. 2B. The embodiment of FIG. 2C. allows a balloon anchored PEG to be trimmed to size because the inflation valve will be located proximal to the balloon.

Feeding lumen 4 may comprise either an internal valve, a cap, a clamp or an external pinch valve. The external valve may be integral with external bolster 15 of PEG system 1. External bolster 15 may serve as both a positioning mechanism for PEG system 1 and a pinch valve. Application of bolster 15 around body 10 allows body 10 to be pulled taut through the patient's abdomen, securing internal bolster 12 against the inner stomach wall of the patient. FIG. 3 illustrates the assembly of the PEG system 1 including the external bolster 15 as positioned in the body of a patient. Body 10 of PEG system 1 passes through external bolster 15, exterior abdomen 46, peritoneum 48, peritoneal cavity 49 and into the internal stomach cavity 52 of the patient. Internal bolster 12 rests softly against interior stomach wall 54. Fistula 19 is typically formed of granulomous, fibrotic and healthy tissues. As a direct access port to the internal abdomen and stomach of the patient, it is imperative that feeding port 4 remains closed when not in use. Feeding port 4 may include a sealing cap 11 to further prevent entry and exit of unwanted microbes, fluids or gases. This cap may be a component of external bolster 15. Additionally, feeding port 4 may have a locking system, such as a luer lock, to ensure direct delivery of the feeding or medicinal fluid to PEG system 1.

As stated above, body 10 of PEG system 1 includes a lumen 4 for administering fluids to the body of a patient. Body 10 is generally cylindrical in cross-section and has an outer diameter of 4 mm–10 mm or approximately 7 mm and a length of 7 in.-12 in. or approximately 9 in. Body 10 has a wall thickness of 2–3 mm. Body 10 may be made of any number of biocompatible polymers such as silicone. Other possible materials include PEBAX® resin, C-Flex® resin, Tycoflex™ resin and such polymers as are well known in the art. The key to the material choice is to offer a soft compliant tube having enough hoop strength and kink resistance to maintain the patency of PEG system 1 during constant use over a long period of time.

Figure 4:
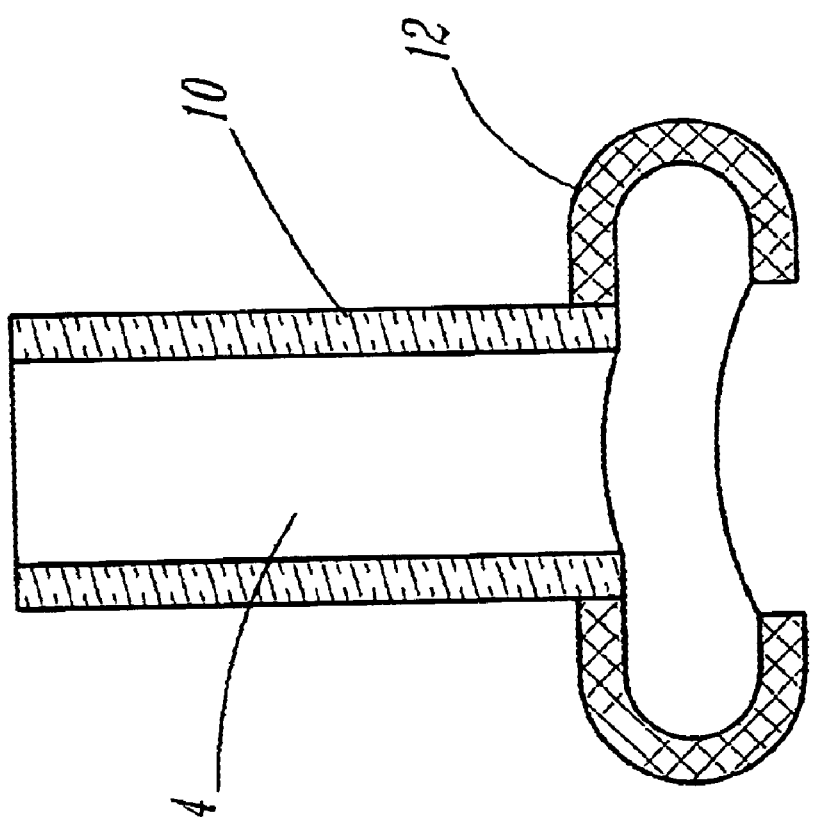
FIG. 4 Illustrates a cross-section of one embodiment of the invention.

Internal bolster 12 is located near the distal end of PEG body 10. The internal bolster 12 is the component of the PEG system that anchors the distal end of the PEG system 1 internal to the stomach of the patient. It is typically constrained to a low profile state during delivery of the PEG device. After introduction into the patient's stomach, bolster 12 is expanded or allowed to expand to effect the axial anchoring of the PEG device. Internal bolster 12 may be any of the bolsters that are commonly used in the art including balloons, collapsible disks or triangles, toroids and any number of shape/material combinations that allow for a low profile delivery and a large profile deployment. Balloon bolsters are the most commonly used. Toroidal bolster 12 as illustrated in the cross-section of FIG. 4 is embodiment known to have in situ durability and low profile delivery and it is well suited for a replacement PEG system.

Bolster 12 would typically have a deployed diameter of 2 cm and would be centrally located around the axis of body 10. Bolster 12 is shown in a deployed configuration in FIG. 4. The wall thickness of the deployed bolster is typically 0.5 mm–2.0 mm which, when folded around the body 10 during delivery, adds only a small increase to the body outer diameter. When a balloon bolster is used, the typical diameter range of the inflated is 1.5 cm–3.0 cm and 2.0 cm on average. The balloon may have a length along PEG body 10 of approximately 2.0 cm Bolster 12 may be an integral component of body 10. The attachment of bolster 12 to body 10 may be accomplished by molding, melting, adhesives or other joining techniques or bolster 12 may be an extension of PEG body 10 as illustrated in FIG. 4.

Referring back to FIG. 1A, PEG system 1 is shown to further include sheath 18 over internal bolster 12 and along the length of PEG body 10. Usually, when a balloon bolster is used, there is no external sheath 18. Sheath 18 is slidably positioned over body 10 and is movable along the axis of the body. Sheath 18 is generally a cylindrical polymeric extrusion. The purpose of sheath 18 is to constrain the bolster 12 to a very low profile during PEG system delivery and then allow a complete release of internal bolster 12 upon withdrawal of the sheath. The sheath 18 is withdrawn proximally along the body. Once bolster 12 is released, bolster 12 expands fully either by virtue of its elasticity and shape or it is expanded by inflation in the case where the bolster is a balloon. Sheath 18 typically has an inner diameter which is slightly larger than the diameter of body 8 plus folded bolster 12 or approximately 2.0 mm wider than the outer diameter of the PEG body 10. The outer diameter of sheath 18 is 2.0 mm–4.0 mm larger than PEG body 10. The sheath material may be any of the materials commonly known in the art including, but not limited to polyethylene and nylon, but may be polyethylene for its clarity, rigidity and lubricity or low coefficient of friction with the body. Sheath 18 extends the full length of the PEG system 1.

In accordance with the present invention, a tip 16 is provided to ease placement of the PEG system 1. Referring now to FIG. 5, some embodiments for the tip 16 of the present invention are illustrated. The tip of the present invention provides for the dilation of tissue during insertion of a PEG system, especially when replacing an existing PEG system with a new PEG system. Dilation is facilitated by providing a tip that varies in diameter from the front end to the back end of the tip.

Figure 8C:
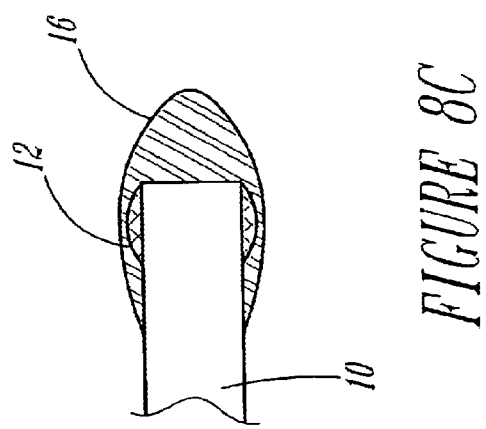
FIG. 8 Illustrates an alternate embodiment of the tip component of the invention.

The material for tip 16 may include any number of biocompatible materials. Embodiments of tip 16 include dissolvable materials, non-dissolvable materials or a combination thereof. Embodiments incorporating a dissolvable material may include poly-glycolic acid, poly-lactic acid, poly-caprolactone, collagen, gelatin, polyvinyl alcohol or any other biocompatible and biodegradable or dissolvable material known in the art. According to one embodiment, the material for tip 16 is gelatin. The choice of a dissolvable material is dependent upon the removal technique designated for dilating tip 16. The solvent for a dissolvable material is typically saline. However, the material may dissolve only in the presence of a specific solvent. Such specific solvents include warmed saline or a pH regulated solvent, such as an acid. It is understood that the solvent may be any biocompatible fluid which helps to remove tip 16. The tip need not dissolve rapidly, if at all. If the tip is to dissolve from body contact in a short period of time, different materials would be used than if the tip is to dissolve over the course of a few hours. In one embodiment, tip 16 is a tip that will be dislodged or removed due to inflation of a balloon bolster or expansion of a toroidal bolster, as no further dislodging is necessary. Coating the balloon and PEG body 10 with a gelatin tip would enable this embodiment as is illustrated in FIG. 8C.

In addition to the dissolvable materials described above, the tip may be constructed using a non-dissolving, biocompatible material such as polyethylene. In this case, the tip must be intentionally removed upon deployment of the PEG system, such as by inflation of balloon bolster 12, or must be held in place by a dissolvable or actuatable component or joint non-dissolving tip materials include, but are not restricted to nylon, polyethylene, polyethylene terephthalate, PEBAX® resin, polyvinylchloride and other biocompatible polymers know in the art The non-dissolving tip should be made of a material and geometry so as not to irritate or injure the digestive tract as it passes naturally through the patient's gastrointestinal system. Preferably, there would be no sharp or abrupt edges on the removable tip and it is lubricious.

Figure 5D:
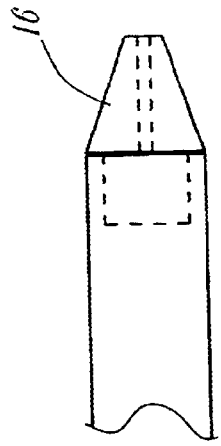
FIG. 5 Illustrates a number of embodiments for the tip component of the invention.
Figure 5E:
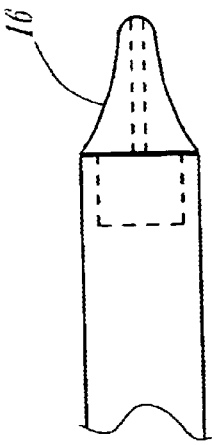
Figure 5A:
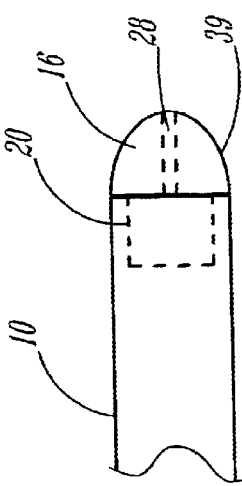
Figure 5B:
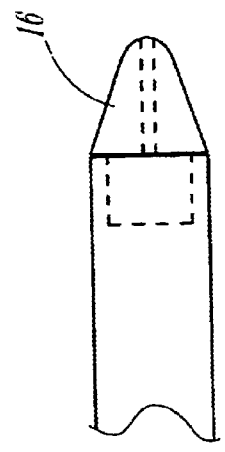
Figure 5C:
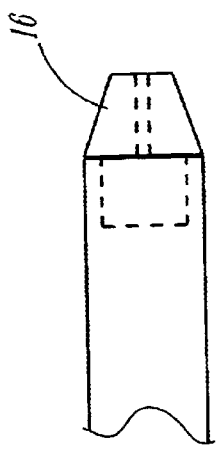

FIGS. 5A through 5D illustrate a number of embodiments for temporary, dilating tip 16. By the nature of dilation, the most distal end 39 of the tip 16 would be of smaller diameter than a more proximal portion 20 of the tip, which is abuts the distal end of body 10. The larger diameter, located at the abutment with the distal end of body 10, is approximately equal to the outer diameter of body 10. Tip 16 may have a larger diameter than PEG body 10 to allow further dilation of the fistula upon advancement. The most proximal section of tip 16 connects to body 10. There are three key components to a dilating tip: tip entry profile, dilation transition profile and tip length. In one embodiment, the entry profile is a rounded tip, as illustrated in FIGS. 5A, 5B and 5E. The dilation transition may be straight as illustrated in FIGS. 5B, 5C and 5D. The tip length may be intermediate, as seen in FIGS. 5B and 5C. FIG. 5A illustrates a tip embodiment having a blunt, round tip with a short taper and short length similar to a bullet. FIG. 5B illustrates a tip embodiment having a short round tip followed by a taper to the large diameter. FIG. 5C illustrates a tip embodiment having a frustoconicular tip of short length and medium taper. FIG. 5D illustrates a tip embodiment having a frustoconicular tip long length and having a long taper. FIG. 5E illustrates a tip embodiment having a nipple shaped tip. Any combination of the parameters of tip length, taper length, and tip entry geometry or presentation can be conceived as being within the spirit of the dilating tip of the present invention. A typical tip would be 5B, having a rounded presentation to the tissue upon entry and a medium taper. It is understood that other variations of the dilating tip will fall within the spirit of the present invention. Tip 16 is joined to body 10 at the distal end of body 10 to create a leading end to PEG system 1. Tip 16 is temporary and it may either be removed due to user intervention, as a result of acute interaction with the body or as a result of digestion by the stomach. The tip of the present invention is removed only following placement of the PEG system 1 into the body of a patient.

In addition to the features described above, tip 16 may be inserted over a guidewire as is illustrated in FIG. 13. In one embodiment of the present invention, a guidewire 29 is normally used. With a guidewire compatible system, the tip may have lumen 28 connecting through the tip and into lumen 4 to allow PEG system 1 to be deployed over a guidewire. Typically, an endoscopic guidewire has an 0.038" diameter. For a PEG placement procedure, the guidewire length may be at least twice the PEG system length or approximately 80 cm in length, although any reasonable length of guidewire may be used. According to one embodiment, the tip would have a 0.040–0.042 diameter hole and lumen extending along the axis from the most distal tip to the proximal end of tip 16, creating a complete guidewire lumen 28 through tip 16. Lumen 28 allows advancing of PEG system 1 over the guidewire without substantially leaving the axis of the guidewire. Guidewire lumen 28 may be located off center. A so-called rapid exchange system includes a guidewire lumen that does not extend the full length of the delivered catheter and may require a guidewire entry lumen that is proximate to the distal end of the catheter delivered. A rapid exchange embodiment permits the guidewire to enter and exit the catheter over a short segment of the length of the catheter, thus requiring a shorter length of guidewire. The rapid exchange system rides mostly adjacent to the guidewire. If no guidewire is used, the PEG system may have a closed tip. Lumen 28 positioned through the dilating tip 16 may allow further procedures to be utilized while the tip 16 is still on the PEG system. Such procedures include fluid infusion or placement of an optical fiber for visualization.

The tip 16 for PEG system 1 is typically lubricious. That is, the tip would have a low coefficient of friction with respect to the tissues contacting the tip. One embodiment provides a lubricious tip having a material that degrades immediately upon contact with fluid and body tissue. This tip may be pre-wetted, wetted at the site by the practitioner or become wetted from body fluids. The result would be a thin slip layer of dissolved tip material forming at the tip/tissue interface. A tip made of gelatin acts in this manner. The fluid layer would coat the complete fistula track from the external abdomen through the body to the internal stomach wall. Alternatively, if a non-dissolvable tip embodiment or slowly dissolving tip embodiment is used on the PEG system, the tip could be coated with a dissolving substance such as gelatin that remains dry until use. Such a material would allow initial lubricity as well as stiffness to the tip. Additionally, a lubricating fluid may be used as is well known in the art. Fluids such as silicone oil, petroleum jelly, liquefied gelatin, K-Y® brand jelly, hyaluronic acid or proprietary lubricants such as Medi-Glide™ lubricant manufactured by Boston Scientific may provide the desired lubricity. These fluids are biocompatible and may be applied directly to the fistula site, onto the PEG system before insertion or through the PEG and into the fistula at insertion.

If tip 16 is made of a non-dissolvable substance, the tip may be fabricated from a material that is lubricious in with respect to body tissues, such as teflon or polyethylene. Tip 16 may include a coating to impart the lubricity to the tip material. One common family of polymers used for this purpose are known as hydrogels. Hydrogels are polymers that readily absorb fluids, rendering them lubricious. With respect to all of the tip embodiments contemplated, the surface of the tip is smooth to prevent any additional friction or catching of tissue during PEG system advancement.

According to another aspect of the present invention, the tip 16 has medically advantageous agents integral to or applied to it prior to insertion or deployment. These agents are used to treat or prevent various pathologies associated with PEG insertion and usage. The agent is deposited along the length of the fistula as the PEG system 1 is inserted into the body. The most common complication associated with PEG usage is infection. Bacteria or microbes may be able to enter the fistula on the outer surface of PEG body 10 and follow the tube into the body. One family of agents includes anti-microbials. Silver ions, salicylic acid, triclosan or antibiotics may be incorporated into the tip, the coating or the lubricating fluid that is applied to the PEG site. The forward advancement of PEG system 1 into the fistula would carry the applied agent along the fistula tract and permit the treatment to be located along the fistula and next to the inserted PEG. The agent could also be applied to PEG body 10 to further enhance its effects on the PEG site. Other families of medically advantageous agents include antiseptics, clot promoting agents, anesthetics and wound healing agents. It is understood that the invention is not limited as to the types of agents that may be applied. The agent could be delivered in such a manner as to act quickly, to act over a period of time or both.

Figure 6F:
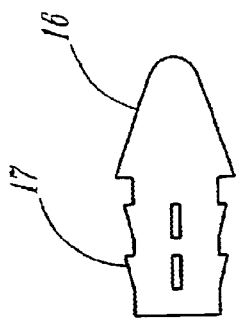
FIG. 6 Illustrates further embodiments for the tip component of the invention.
Figure 6C:
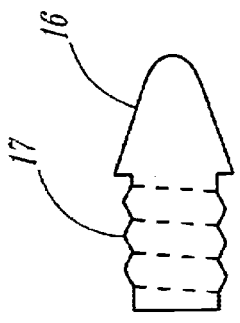
Figure 6A:
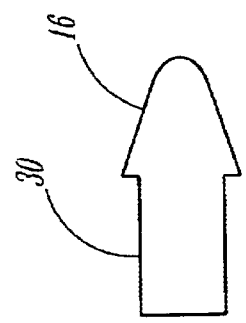
Figure 6G:
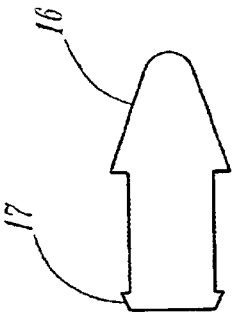
Figure 6D:
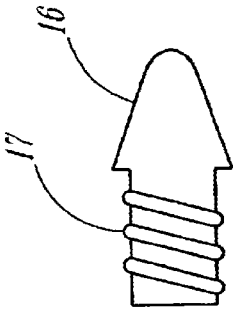
Figure 6B:
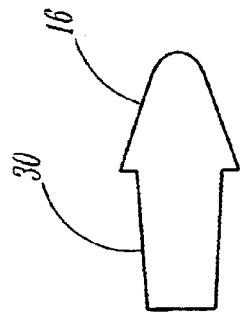

Referring now to FIGS. 6A–6E a number of embodiments for attaching tip 16 to the PEG body 10 are illustrated. These tips operate by creating an interference fit between the outer surface of tip 16 and the inner surface of lumen 4 in body 10. Alternatively, body 10 may contain engaging mechanisms inside lumen 4 or on the outside surface of body 10 to retain tip 16. One form of attachment is an interference fit between proximal portion 30 of tip 16 and inner lumen 4 of PEG body 10. One embodiment is illustrated in FIGS. 6A and 6B which provides for a rounded, tapered tip with a circular attachment of reduced diameter that can be inserted into lumen 4. The attachment 30 length is approximately 1.0 cm and allows the PEG system to follow a curved path within the fistula and through to the stomach without dislodging tip 16 along the fistula. The attachment portion 30 may operate by either a friction fit between tip 16 and PEG body 10 or by engaging the lumen with external protuberances 17 as illustrated in FIGS. 6C–6G.

Figure 6E:
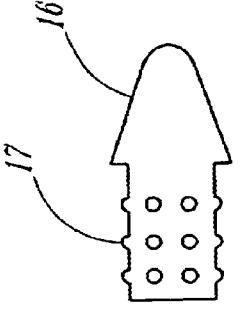

The proximal end of the tip in FIG. 6B is similar to the proximal end of the tip in FIG. 6A with the exception that the attachment portion 30 of FIG. 6B is tapered to allow easier insertion of tip 16 into lumen 4 during securement of tip 16 into PEG system 1. The tip embodiments illustrated in FIGS. 6C and 6D provide for the attachment end 30 to have ribs or threads to secure it within lumen 4. These embodiments form a mechanical lock between the lumen 4 and the tip 16. Threads have the advantage of allowing the tip to be screwed into place when added to PEG system 1. FIGS. 6E–6G illustrate alternate embodiments for creating protuberances 17 on attachment portion 30. FIG. 6E illustrates one embodiment wherein tip 16 has many small bumps covering attachment portion 30. FIG. 6F illustrates another tip embodiment wherein the protuberances 17 are barbs. FIG. 6G illustrates yet another embodiment wherein there is only one protuberance 17 at the proximal end of tip 16.

An alternate embodiment for tip 16 includes a combination of dissolvable and non-dissolvable materials, FIGS. 7A, 7B and 7C illustrate three embodiments wherein a component of the tip 16 dissolves to release the rest of the tip from the attachment with body 10 of PEG system 1. In one composite embodiment, illustrated in FIG. 7A, the tip 16 has a non-dissolvable core and a dissolvable annular surface component resting on attachment 30. Following deployment of PEG system 1, removal of tip 16 is promoted by the dissolution of outer material 36 in response to either body fluids or fluid applied by the practitioner. FIG. 7B illustrates an alternate embodiment wherein the core of tip 16 is dissolvable and carries an outer ring 42 that is made of a thin non-dissolvable elastomere, such as silicone. This tip responds to natural or practitioner provided fluids to cause dissolving at the core. As the tip dissolves, outer ring 42 shrinks elastically until the interference fit between it and lumen 4 has been removed. When the interference is gone, the tip will fall out. FIG. 7C illustrates an alternate embodiment wherein a dissolvable adhesive 43 attaches tip 16 to body 4. The adhesive is dissolved by the practitioner or by body fluids. In all composite embodiments, the non-dissolvable components are passed naturally through the patient's GI tract.

Figure 8A:
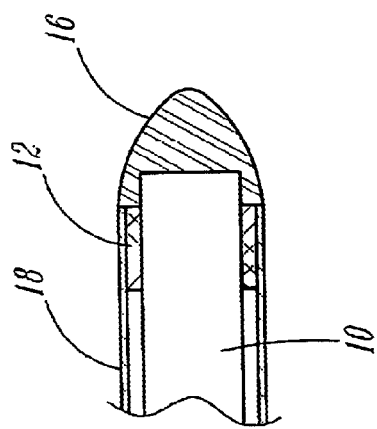
Figure 8B:
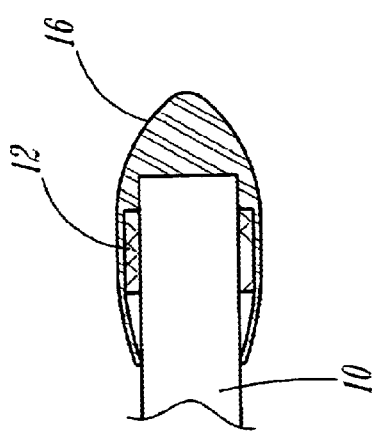

Tip 16 may be a cap surrounding distal end of PEG body 10 as illustrated in FIG. 8A. The whole cap or the cap lip in contact with body 10 may dissolve, dropping the tip off of the PEG system. It is possible that the cap does not dissolve, in which case the tip would be forced off by the practitioner. FIG. 8B. illustrates an embodiment wherein tip 16 serves to retain internal bolster 12 upon delivery of PEG system 1, rather than by use of the external sheath 18 as illustrated in FIGS. 1 and 2. FIG. 8C illustrates an embodiment of a PEG system wherein bolster 12 is a balloon and the balloon is coated with a material that serves to retain the bolster and as a dilating tip. The tips illustrated in FIGS. 8B and 8C may be removed by inflation of the bolster following placement of the PEG system. These tip would either break apart or expand enough to fall off the PEG system. FIG. 8D illustrates an embodiment having tip 16 attached to the body by use of a frangible heat shrink tube 15. Heat shrink 15 overlies balloon bolster 12 and tip 16. When the balloon is inflated, the heat shrink breaks apart and falls off, dropping tip 16.

Figure 9D:
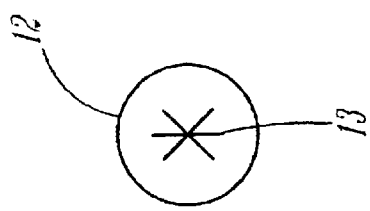
FIG. 9 Illustrates an alternate embodiment of the tip component of the invention.
Figure 9C:
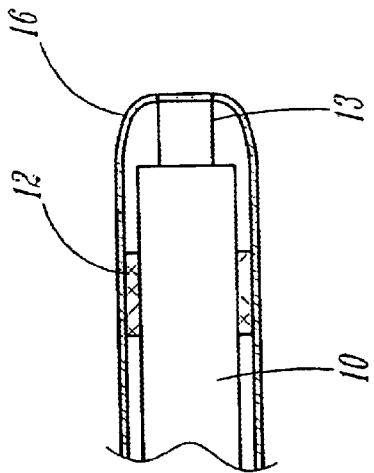
Figure 9A:
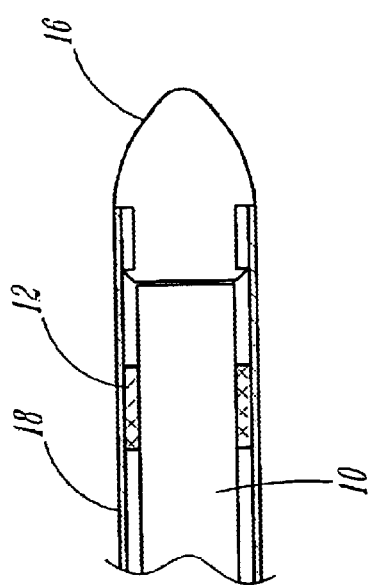
Figure 9B:
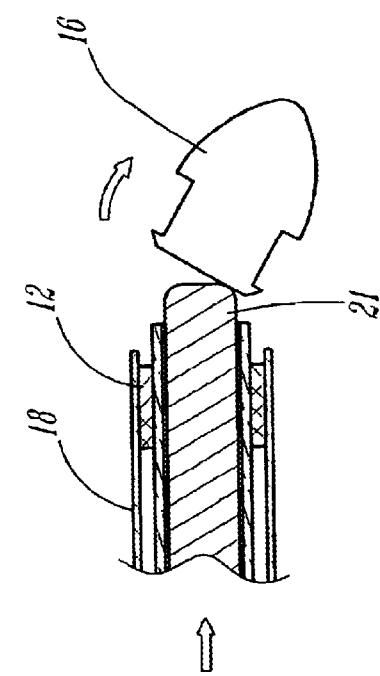

Tip 16 may also be connected to the distal end of sheath 18 that is used to cover the internal bolster 12. Sheath 18 is used to retain bolster 12 which is typically not a balloon if the sheath is utilized. Tip 16 may be attached to an extension of sheath 18 that would reach beyond the bolster as illustrated in the embodiment of FIG. 9A. Tip 16 is similar to any of the above tip embodiments in shape, material and attachment; see FIGS. 5 and 6. One embodiment of a tipped sheath has tip 16 fitted within the distal end of sheath 18. When practitioner intervention is the mode of tip removal, a stiffening mandrel 21 may be necessary to steady the PEG body 10 as sheath 18 is withdrawn from the system as illustrated in FIG. 9B. In one embodiment having a tipped sheath, tip 16 could be a tapered extension of the front end of the sheath 18, as seen in FIGS. 9C and 9D. This taper is expandable upon retraction of the sheath, by virtue of axially aligned cuts in the wall of the tapered portion of sheath 18.

The sheath is retracted following delivery of the PEG into the stomach. The embodiment of FIGS. 9C and 9D may require temporary stiffening of the PEG system from a removable mandrel as that illustrated in FIG. 9B.

Figure 10C:
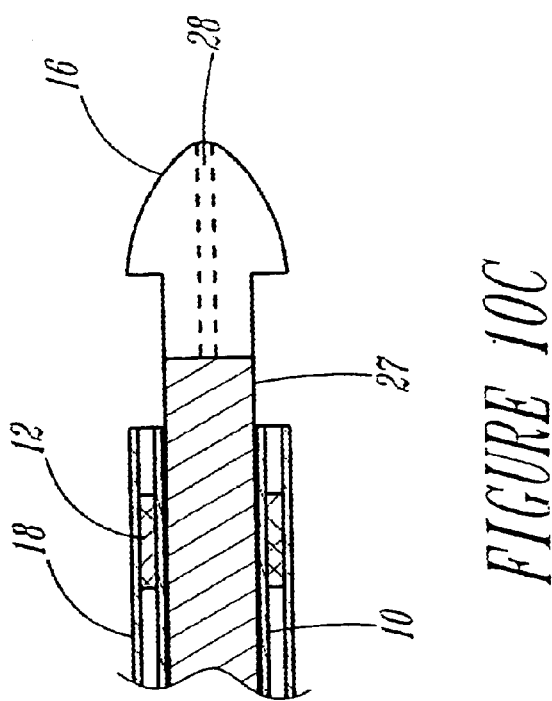
FIG. 10 Illustrates an alternate embodiment of the tip component of the invention.
Figure 10A:
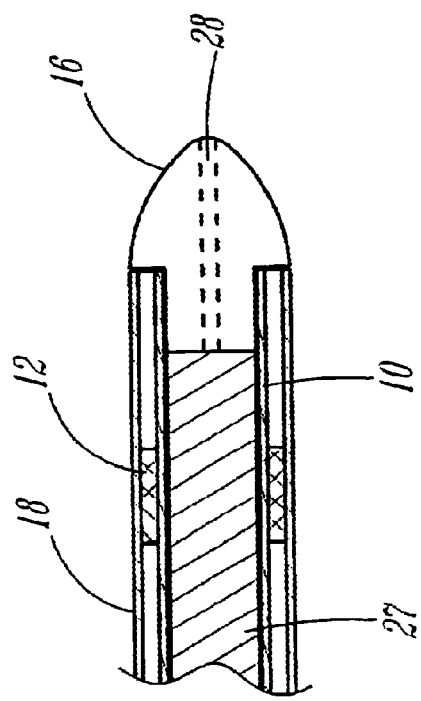
Figure 10B:
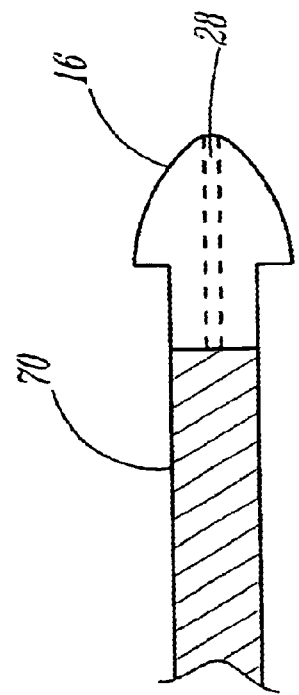

Tip 16 may also be a component of stiffening mandrel 27 as illustrated in the embodiment of FIGS. 10A, 10B and 10C. In this embodiment, the PEG system would be prepared by insertion of the proximal end of mandrel 70 with tip 16 into the distal end of the PEG system. This mandrel is placed in a reverse manner, from the distal end to the proximal end, through PEG system 1 until tip 16 abuts the distal end of PEG body 10. The practitioner then advances PEG system 1 into the fistula either over a guidewire or without a guidewire. If guidewire delivery is used, the mandrel would have an internal lumen, such as a hypotube has, that is aligned with the guidewire lumen 28 in tip 16. The tip is dislodged from the stiffening mandrel by tugging proximally on the rod. This tugging forces the tip against the PEG system and causes the tip to fall off. In an alternate embodiment, the mandrel has a dissolvable tip attached. In a further alternate embodiment, the tip may be attached to the stiffening mandrel by a dissolvable adhesive. As is understood, the tip and attachment may be equivalent to any of those disclosed above. Tip 16 can be induced to fall off by any of the above mentioned manners.

Figure 12A:
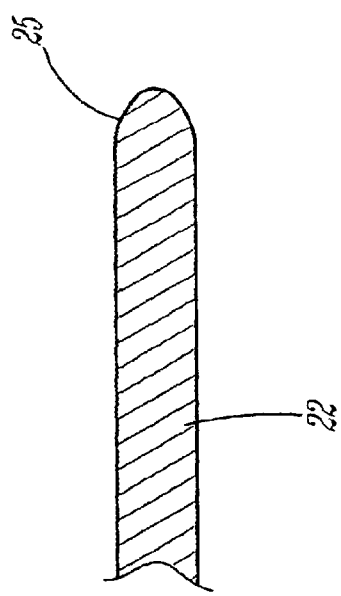
FIG. 12 Illustrates an alternate embodiment of the invention.
Figure 12B:
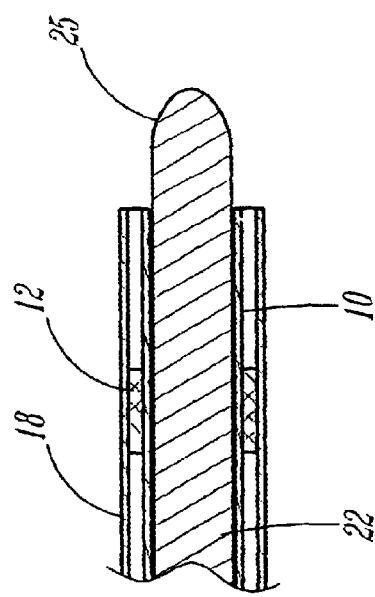
Figure 12C:
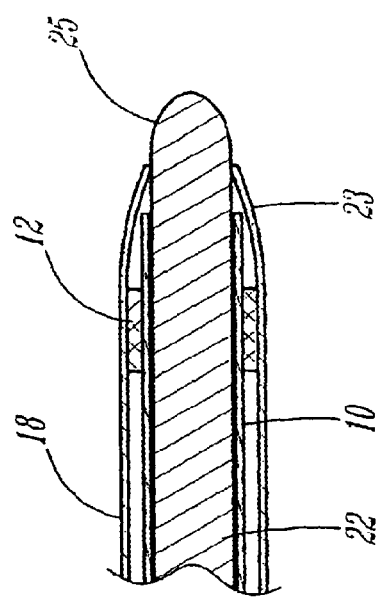

A similar embodiment to that of FIG. 10 is illustrated in FIG. 12. FIG. 12A illustrates a stiffening mandrel 22 with a tapered tip 25. Stiffening mandrel 22 is placed in lumen 4 of PEG system 1 to a point where tapered tip 25 extends far enough out the distal end of body 10 to act as an entry dilator for PEG system 1 as illustrated in FIG. 12B. FIG. 12C further illustrates an embodiment wherein sheath 18 of PEG system 1 is tapered as well. Taper 23 of sheath 18 tapers to meet the diameter of stiffening mandrel 22 and provide as much of a continuous taper as possible from tip of stiffening mandrel 22 to the distal end of body 10. Stiffening mandrel 22 may have a guidewire lumen internal to allow PEG system 1 to be delivered over a guidewire. Stiffening mandrel 22 as well as mandrel 21 of FIG. 10 and mandrel 70 of FIG. 9 may comprise any material including metals or plastics.

Figure 14A:
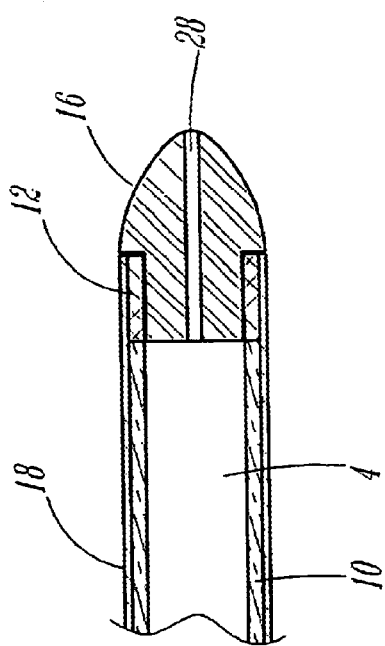
FIG. 14 Illustrates an alternate embodiment of the invention.
Figure 14B:
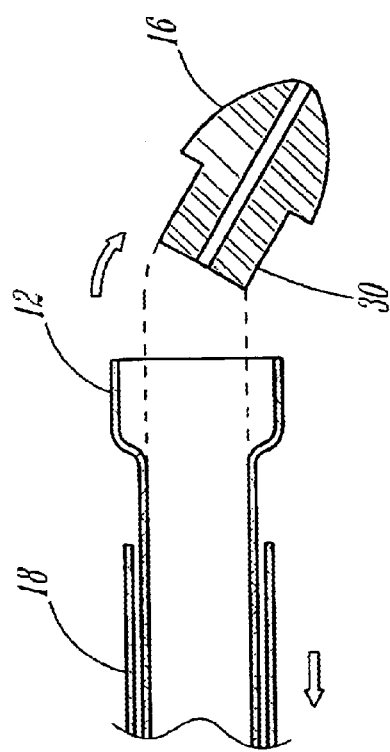

FIGS. 14A and 14B illustrates yet another mode of attachment of dilating tip 16 to PEG system 1. In this embodiment, tip 16 is retained by virtue of the compression of bolster 12 and PEG body 10 under sheath 18. The inner diameter of bolster 12 is greater than the outer diameter of attachment 30 of tip 16. Attachment 30 rests secure within compressed bolster 12. However, removal of sheath 18 allows bolster 12 and PEG body 10 to expand to their deployed configurations and allows tip 16 to fall off. One bolster 12 for this embodiment is a toroidal bolster as illustrated in FIG. 4.

Having described various embodiments of the PEG system of the present invention, a description of its use is provided. This PEG system 1 of the present invention may be used in a replacement PEG procedure, but may also be used during the initial PEG placement. A replacement PEG is one that is placed into the existing fistula that is left after removal of an initial PEG system. If PEG system 1 is used during an initial placement, percutaneous access to the stomach is performed prior to introducing the PEG system.

One embodiment of the process for replacement of a PEG system with a dilating tip is illustrated in FIG. 11. As described above, the initial PEG system 1 resides within the patient's abdomen and extends from the patient's exterior abdomen 46, through the peritoneum 48 and peritoneal cavity 49 and into the stomach cavity 52, as is illustrated in FIG. 11A. FIG. 11B illustrates that initially, external bolster 15 is removed from the existing PEG system. The internal bolster 12 rests up against internal stomach wall 54. The PEG is usually removed by a practitioner, who places the palm of his hand flat around the PEG entry site with his fingers 60 splayed about the PEG body 10, as is illustrated in FIG. 11C. While holding the abdomen down, the practitioner pulls sharply upwards on the implanted PEG body. This action causes the tube to begin to move outwardly and the internal bolster folds in on itself; reducing its profile as it moves into the fistula. Alternatively, if the internal bolster 12 is a balloon, the balloon may be deflated by use of a syringe attached to the inflation valve at the proximal end of the PEG system. The PEG is pulled, in full, through the fistula and out of the body.

Figure 11A:
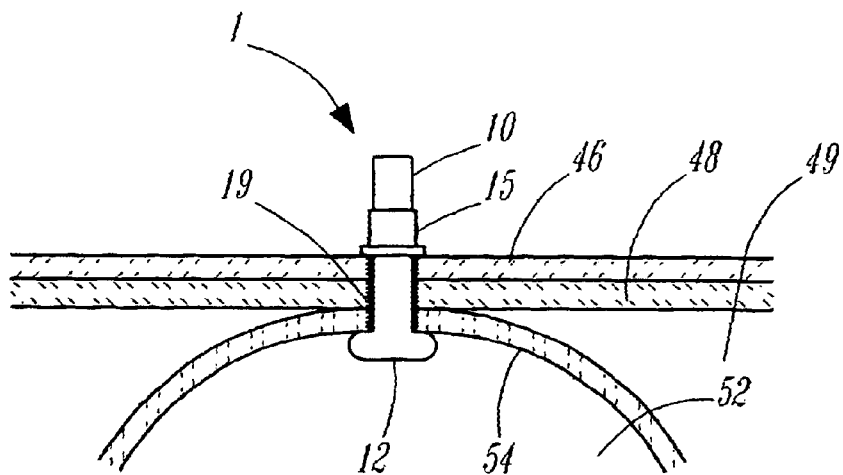
FIG. 11 Illustrates an alternate embodiment of the tip component of the invention.
Figure 11B:
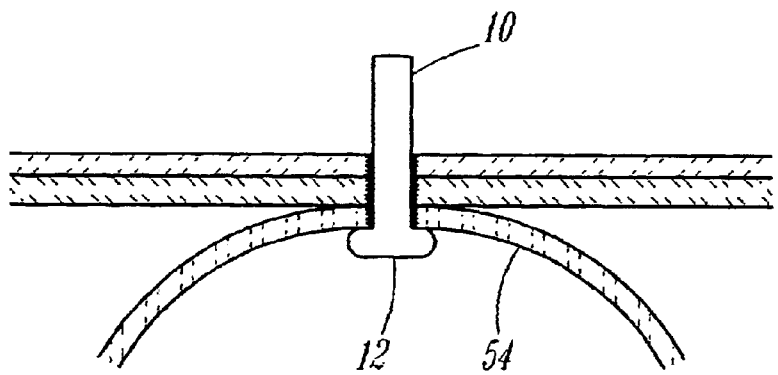
Figure 11C:
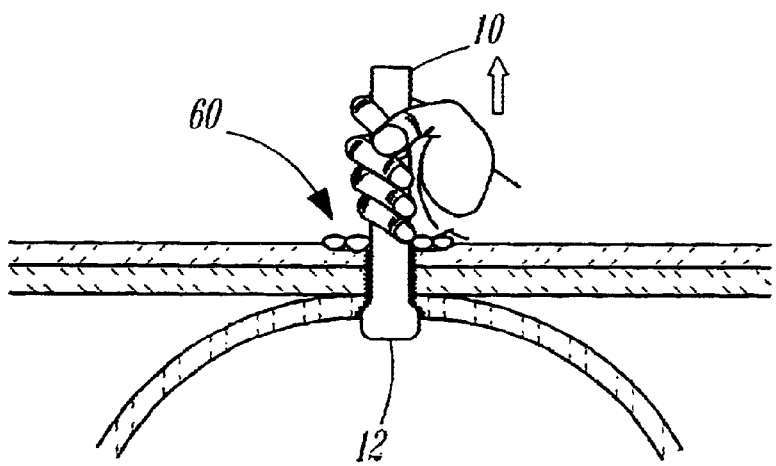
Figure 11D:
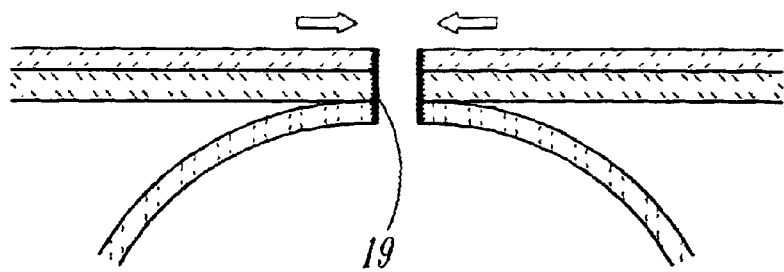
Figure 11E:
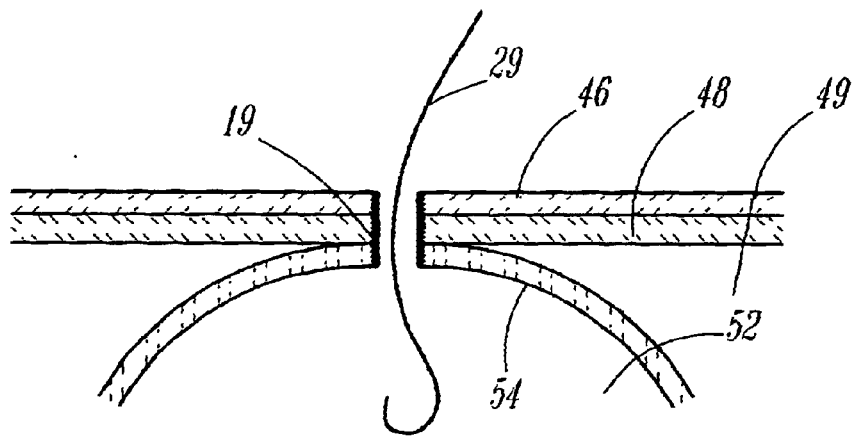
Figure 11F:
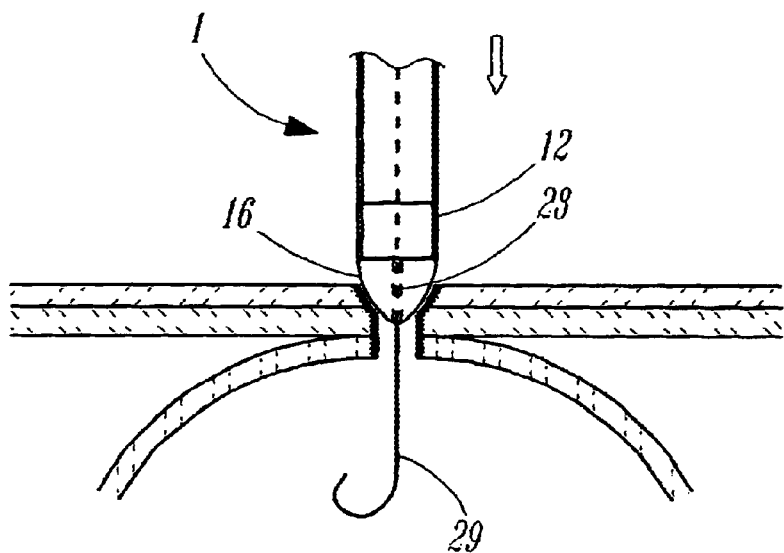

FIG. 11D illustrates the condition of fistula 19 when the initial PEG system has been removed and the fistula begins closing in on itself. This is a natural wound healing reaction. FIG. 11E illustrates the step wherein following PEG removal, a guidewire 29 is inserted into the fistula 19 and finally into the stomach cavity 52. Alternatively, the guidewire may be placed into the initial PEG system before removal and the guidewire position is maintained while the initial PEG system is removed. Care must be taken to ensure that the guidewire is placed accurately into the stomach, as it may veer off course and situate itself into the peritoneal cavity. A practitioner may use fluoroscopy to check the correct position of the guidewire. With the guidewire 29 safely in place and extending external to the body, replacement PEG system 1 is placed over the guidewire, through the fistula and into the stomach, as is illustrated in FIG. 11F. Placing the PEG system over a guidewire simply comprises aligning lumen 28 in the tip 16 of PEG system 1 over the guidewire and advancing the PEG forward while holding the proximal end of the guidewire firmly so as not to lose the position of the guidewire.

Figure 11G:
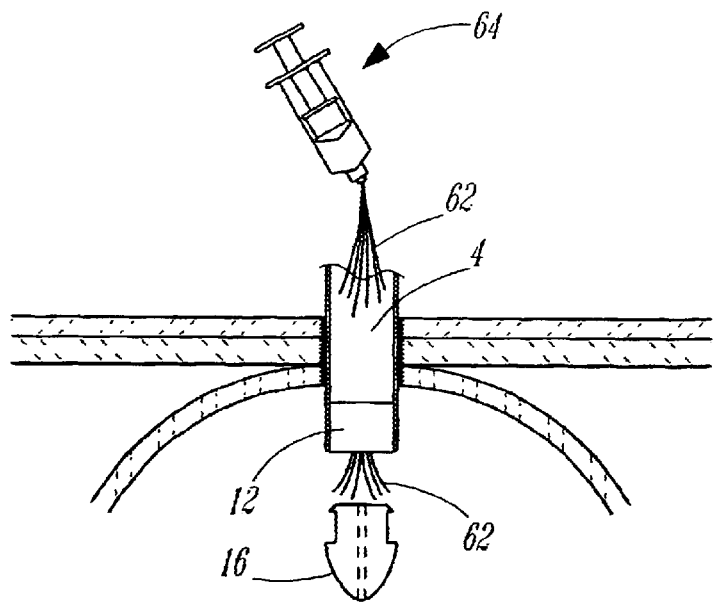
Figure 11H:
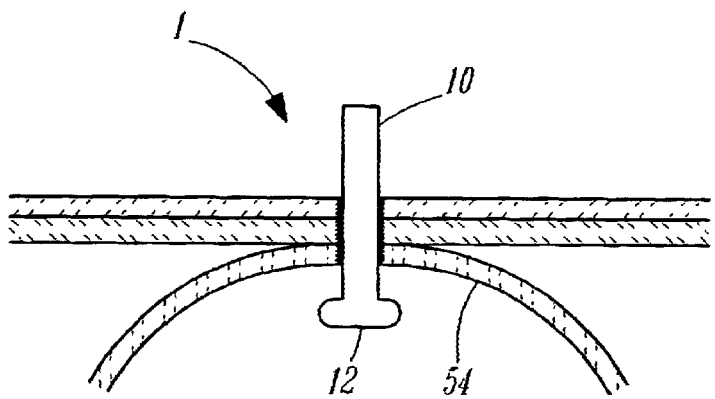
Figure 11I:
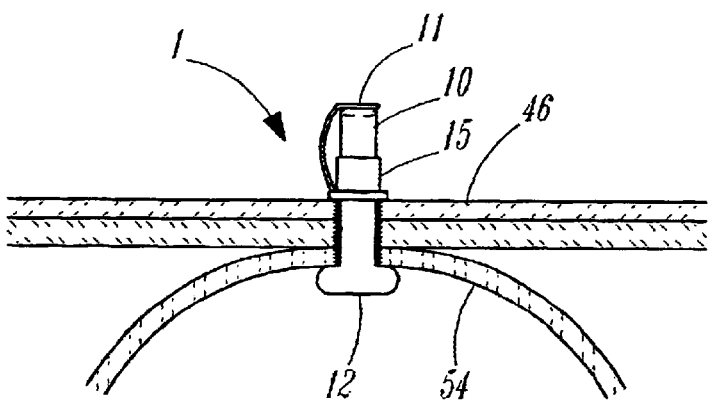

Once the PEG is inserted and the position confirmed, guidewire 29 is removed. Next, tip 16 is removed, usually by practitioner intervention. FIG. 11G illustrates the step of applying saline 62 from syringe 64 to enforce the removal of tip 16. Saline 62 aids removal of tip 16 by pneumatic pressure as well as by creating a fluid layer between the tip and inner lumen 4. If tip 16 is dissolvable, the saline initiates that process. FIG. 11H illustrates the step of deploying internal bolster 12 is deployed. The deployment of bolster 12 may either be by inflation of the balloon, by removal of the sheath that covers the bolster, or by any other the methods as described above, depending on the embodiment of bolster 12 used. With the internal bolster 12 deployed, PEG body 10 is tugged gently to seat itself against the internal lining 54 of the stomach. FIG. 11I illustrates the step wherein external bolster 15 is fitted around the body 10 of the PEG system 1 and positioned against the exterior abdomen 46. The external bolster may have a cap 11 included to fit into or around the open lumen of the feeding port 4. The amount of tension on the PEG body 10 is adjusted by the location of the external bolster. After completed deployment, guidewire 29 is removed. PEG body 10 is then cut to align itself with the external bolster and a cap 11 is placed into the proximal end of lumen 4 to maintain a sterile yet accessible lumen.

As an alternative to using saline to remove tip 16, a physician may chose to use a mandrel within lumen 4, similar to the mandrels 21, 22 and 27 illustrated in FIGS. 9, 10 and 12. Using a mandrel, tip 16 may be pushed forward into stomach cavity 52. The practitioner may choose, alternatively, to remove the tip by use of a medical instrument delivered through the endoscope. Such an instrument would have an actuator at the proximal end, a body to extend into the body of the patient and an effector at the distal end. The effector in this case would be any type of tool that could grab or capture at least part of the tip. The instrument is actuated at the proximal end such that the effectors would be operated remotely. These allow the practitioner to snake them into the body through a percutaneous lumen or, more often, through an endoscope, as direct viewing facilitates such procedures. If the procedure is being monitored via an endoscope, which is placed through the mouth and esophagus and into the stomach, the practitioner may chose to pull the tip off with endoscopic graspers, forceps or snares.

The practitioner may also facilitate tip 16 removal by the administration of a biocompatible solvent into the stomach via the PEG system or the endoscope. Instead of a solvent, a heated fluid may be administered into the gastrointestinal tract resulting in the softening of at least part of the tip. As well, a solution could be administered. to react chemically with at least part of the tip. One embodiment would be a tip containing a pH sensitive component, which reacts with an acid, or base solution administered to the gastrointestinal tract of the patient. The reaction results in the fractionating and removal of the tip. With the tip removed, the PEG system is ready for normal use. Alternatively, the tip may fall off during digestion.

Dilating tip 16 may be provided as a pre-assembled component of PEG system 1 or as a separate, attachable component. Tip 16 may be provided with PEG system 1 or may be packaged separately. Tip 16 may have embodiments wherein it fits into any number of PEG tube brands and types. Mandrels 21, 22 and 27 may also be packaged with PEG system 1 or separately. These mandrels have embodiments that fit into any brand or type of PEG system as well.

PEG system 1 with dilating tip 16 may also serve as part of a kit for the initial placement or replacement of a PEG. Such a kit may include a guidewire, a stiffening mandrel, a syringe, a percutaneous access system and a scalpel. Tip 16 may be pre-assembled into PEG system 1, be made available in the PEG system kit or be packaged and provided separately. PEG system 1 is also not exclusive to use in the stomach alone. PEG system 1 may be used anywhere along the digestive tract including the small and large intestines and especially the jejunum.

While some specific embodiments of the invention have been described, those skilled in the art will realize that various changes and modifications may be made to the invention without departing from the spirit of the invention, and it is intended to claim all such changes and modifications which fall within the scope of the invention.

What is claimed is:

1. A method for placing a medical device comprising the steps of:

accessing a percutaneous fistula in the abdomen of a patient;

aligning a percutaneous endoscopic gastrostomy device with the fistula, the device having a proximal end, a distal end, and at least one internal lumen extending between the proximal end and the distal end, a tapered and dilating tip, the tip being disposed on the distal end of the device; the tip further having an at least partially dissolvable attachment portion for removably attaching the tip to the device;

advancing the device forward and into the body of the patient and at least partially dissolving the at least partially dissolvable portion of the tip by use of a solvent once the device is in position internal to the body of the patient.

2. The method of claim 1 further comprising the step of removing a percutaneous endoscopic gastrostomy tube from the body of a patient just prior to the step of accessing the percutaneous fistula.

* * * * *